(12) United States Patent
Ritter et al.

(10) Patent No.: US 8,329,842 B2
(45) Date of Patent: Dec. 11, 2012

(54) OPHTHALMOLOGICAL COMPOSITION AND USE THEREOF

(75) Inventors: Helmut Ritter, Wuppertal (DE); Daniel Schmitz, Köln (DE)

(73) Assignee: Arcltec GmbH, Hennigsdorf (DE)

( * ) Notice: Subject to any disclaimer, the term of this patent is extended or adjusted under 35 U.S.C. 154(b) by 78 days.

(21) Appl. No.: 12/746,904

(22) PCT Filed: Dec. 5, 2008

(86) PCT No.: PCT/EP2008/066905
§ 371 (c)(1),
(2), (4) Date: Sep. 13, 2010

(87) PCT Pub. No.: WO2009/074521
PCT Pub. Date: Jun. 18, 2009

(65) Prior Publication Data
US 2010/0324165 A1    Dec. 23, 2010

(30) Foreign Application Priority Data

Dec. 11, 2007   (DE) .......................... 10 2007 059 470

(51) Int. Cl.
*C08F 120/54*   (2006.01)
(52) U.S. Cl. .................................... 526/303.1; 526/319
(58) Field of Classification Search ............... 526/303.1, 526/319
See application file for complete search history.

(56) References Cited

U.S. PATENT DOCUMENTS

| | | | |
|---|---|---|---|
| 2,725,377 A * | 11/1955 | Long et al. ................ 534/802 |
| 3,721,657 A * | 3/1973 | Seiderman ................ 526/217 |
| 3,876,581 A * | 4/1975 | Neogi ...................... 521/62 |
| 4,082,894 A | 4/1978 | Yoshida |
| 4,463,149 A * | 7/1984 | Ellis ........................ 526/279 |
| 4,748,224 A | 5/1988 | Novicky |
| 4,922,003 A * | 5/1990 | DeMartino et al. ........... 560/221 |
| 4,948,855 A | 8/1990 | Novicky |
| 6,612,828 B2 * | 9/2003 | Powers et al. ............. 425/145 |
| 6,887,269 B1 * | 5/2005 | Hampp et al. ............. 623/6.57 |
| 2005/0027031 A1* | 2/2005 | Chang et al. ............... 522/68 |
| 2006/0041067 A1* | 2/2006 | Sugamoto et al. .......... 525/154 |
| 2006/0122349 A1* | 6/2006 | Mentak et al. ............ 526/303.1 |
| 2007/0048349 A1 | 3/2007 | Salamone et al. |
| 2007/0092830 A1* | 4/2007 | Lai et al. .................. 430/270.1 |
| 2007/0092831 A1* | 4/2007 | Lai et al. .................. 430/270.1 |
| 2009/0157178 A1* | 6/2009 | Hampp ................... 623/6.11 |
| 2010/0160482 A1* | 6/2010 | Nachbaur ................. 523/106 |

FOREIGN PATENT DOCUMENTS

| | | |
|---|---|---|
| DE | 69918108 T2 | 7/2005 |
| DE | 102006028507 A1 | 12/2007 |
| DE | 102007059470 B3 | 5/2009 |
| EP | 0068632 A2 | 1/1983 |
| EP | 0231572 A2 | 8/1987 |
| EP | 0321891 A2 | 6/1989 |
| EP | 0383074 A2 | 8/1990 |
| WO | 82/00295 A1 | 2/1982 |
| WO | WO 2007147599 A1 * | 12/2007 |

OTHER PUBLICATIONS

Polymers for in vivo Tuning of Refractive Properties in Intraocular Lenses, Trager et al., Macromolecular Bioscience, first online publication Oct. 19, 2007.*

International Search Report, International Patent Application PCT/EP2008/066904, date of completion May 7, 2009, 6 pages (related to U.S. Appl. No. 12/746,895).

International Search Report, International Patent Application PCT/EP2008/066905, date of completion Feb. 25, 2009, 2 pages.

* cited by examiner

*Primary Examiner* — James J Seidleck
*Assistant Examiner* — Peter A Salamon
(74) *Attorney, Agent, or Firm* — Fitch, Even, Tabin & Flannery, LLP

(57) ABSTRACT

The subject matter of the present invention is an ophthalmologic composition having an UV absorber and a violet absorber, wherein a high transmission is achieved in the blue light spectrum, and an eye implant, in particular an intraocular lens, which is produced with this ophthalmologic composition.

27 Claims, No Drawings

OPHTHALMOLOGICAL COMPOSITION AND USE THEREOF

The invention relates to an ophthalmologic composition as well as the use thereof, in particular as an eye implant (intraocular lens).

It is known that the retina of the eye can be protected from phototoxic influences of radiation in the ultraviolet range (200 nm to 400 nm) and in the violet range of the visible light (400 nm to 440 nm) with the aid of molecular absorbers. Such absorbers can be provided in the optical field for use in intraocular lenses (IOL). Intraocular lenses on the market in particular only partially absorb in the violet light range. With respect to order of magnitude, 25% to 35% of the phototoxic light with a wavelength of 430 nm pass through the conventional lens material.

Studies show that the violet light portion plays a crucial role in the development of an age-related macular degeneration (AMD). It begins with depositions of so-called druses, end products of metabolism (lipofuscins), and can be converted into an areal cell death (geographic atrophy) of the retinal pigment epithelium in the advanced stage.

On the other hand, for the photoreception, in particular for the vision in reduced light conditions (scotopic vision), i.e. in the mesopic and scotopic vision, the transmissibility of the lens material in the blue light spectrum (about 450 nm to 500 nm) is of crucial importance. In this blue wavelength range, as little light as possible is to be absorbed in order to exclude an impairment of the mesopic and scotopic vision. However, IOL on the market have a transmission of only about 70% to 75% in this wavelength range (e.g. at 475 nm).

Therefore, it is the object of the invention to provide an ophthalmologic composition of the initially mentioned type, which ensures a high degree of photoprotection with maximum photoreception at the same time. Thus, this composition has to absorb substantially the entire ultraviolet spectral range and the violet light portion of the visible spectrum, but at the same time allow the complete transmission of blue light, in particular of the wavelength range between 450 nm and 500 nm. According to the invention, this object is solved by the features of claim 1.

The ophthalmologic composition of the invention includes an UV absorber quantitatively absorbing radiation in the wavelength range of about 200 nm to 400 nm. Further, the ophthalmologic composition includes a violet absorber absorbing violet light of the wavelengths of about 400 nm to 430 nm. Suitable chromophore basic structures of the violet absorber are N-alkoxyacrylated or N-alkoxymethacrylated or even N,N-dialkoxyacrylated or N,N-dialkoxymethacrylated nitroanilines.

As an UV absorber, the ophthalmologic composition includes a biocompatible UV light protection agent, for which coumarin derivatives, which are optionally linked to one or more acryl or methacryl functions via alkyl spacers, are used.

Preferably, the composition is constructed exclusively based on acrylate and/or methacrylate.

The object of the invention is explained in more detail in claims 1 to 27.

UV Absorbers

Suitable UV absorbers of the ophthalmologic composition according to the invention are compounds of the following structures:

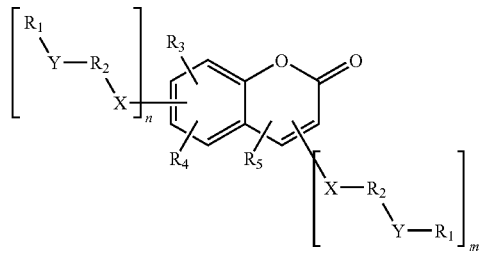

general formula I n=0 to 2 m=0 or 1 wherein n+m≧1

X=O, NH, NR6

Y=O, NH, NR6

R1=acryl or methacryl radical

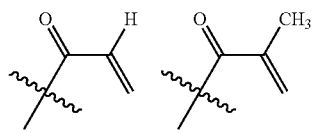

R2=organic alkyl or aryl spacer group (or combination of both) with up to 30 atoms selected from: C, H, Si, O, N, P, S, Cl, Br, F R3, R5, R6=H or organic alkyl or aryl group (or combination of both) with up to 30 atoms selected from: C, H, Si, O, N, P, S, Cl, Br, F R4=only if n=0 or 1: H or organic alkyl or aryl group (or combinations of both) with up to 30 atoms selected from: C, H, Si, O, N, P, S, Cl, Br, F Examples of corresponding structures (all stereoisomers or racemic mixtures are included) are:

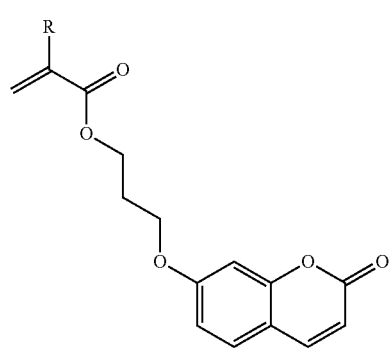

Structure 1

Structure 2

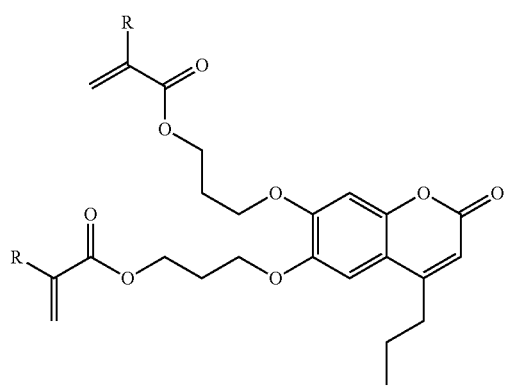

Structure 3

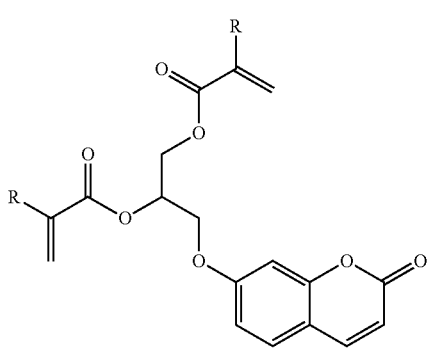

Structure 4

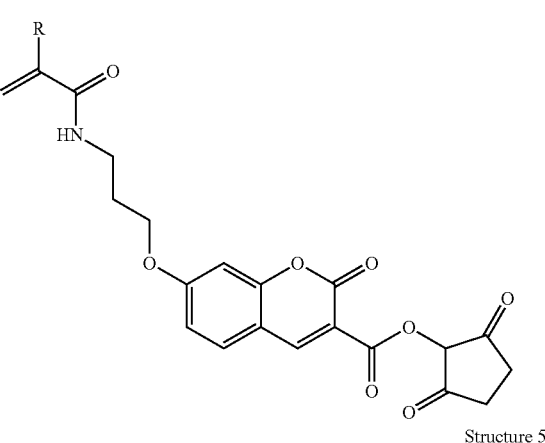

Structure 5

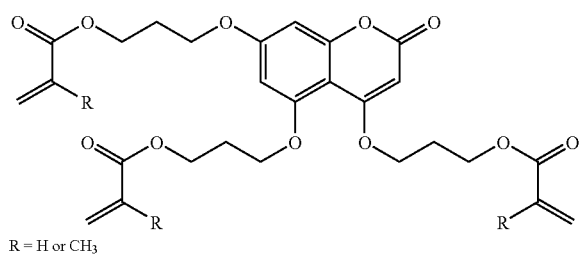

R = H or CH₃

UV absorbers, the basic structure of which is based on the structures 2, 3 and 4, have the advantage that they allow a quantitative incorporation into the lens material due to the presence of plural polymerizable terminal groups, and moreover have cross-linking properties. Thus, in lens manufacture, ideally, the addition of an additional cross-linker can be omitted.

A preferred UV absorber of the ophthalmologic composition according to the invention is:

Coumarin-7-propoxymethacrylate having the structure:

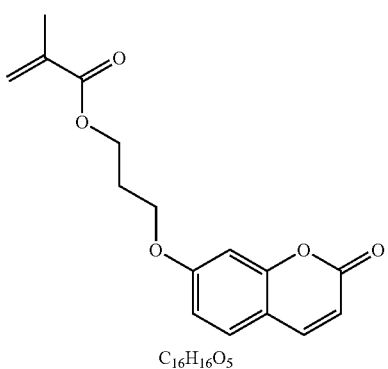

$C_{16}H_{16}O_5$
Molecular weight 288.30 g/mol

The production of this compound is effected in two steps, wherein the 7-hydroxycoumarin is commercially available:

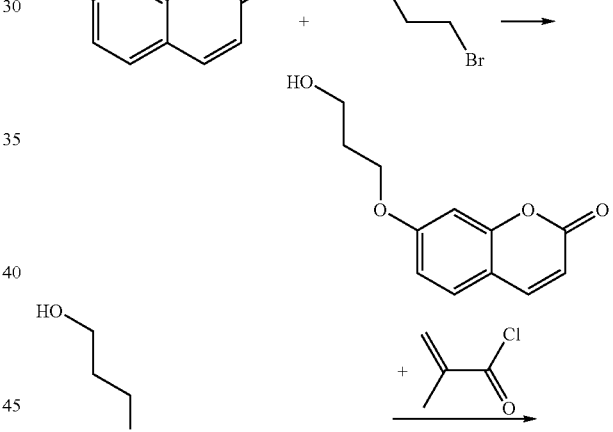

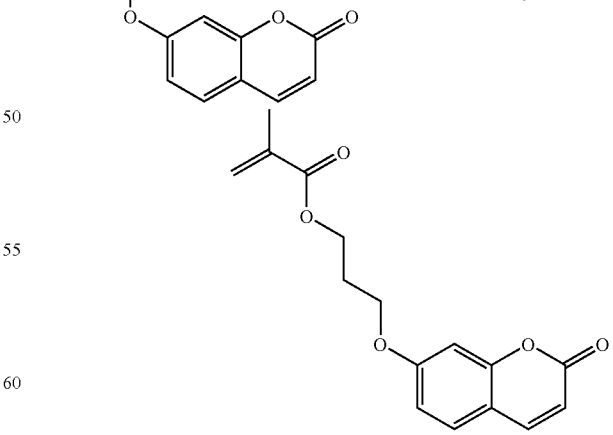

Further embodiments for the UV absorber are compounds, in which a coumarin base body is connected to one or more acryl or methacryl radicals via various spacers. They have the following structure:

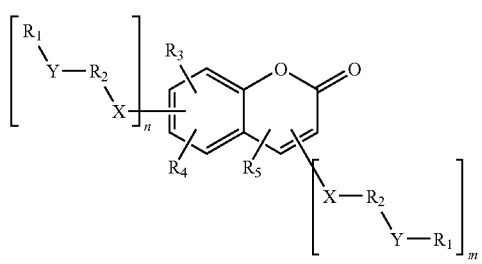

wherein

R1 is an acryl or methacryl radical

R2: organic branched and unbranched alkyl or aryl substituents (or combinations of both) with up to 30 atoms selected from C, H, Si, O, N, P, S, F, Cl, Br R3, R4 and R5: H or organic branched and unbranched alkyl or aryl substituents (or combinations of both) with up to 30 atoms selected from C, H, Si, O, N, P, S, F, Cl, Br X and Y: O, S, NH, NR (R is an organic branched or unbranched alkyl or aryl substituent (or combinations of both) with up to 30 atoms selected from C, H, Si, O, N, P, S, F, Cl, Br n=0 to 2 as well as m=0 or 1, wherein n+m is always greater than or equal to 1

EMBODIMENTS UV ABSORBERS

Example 1 n=2, m=0, X=O, $R_2$=$C_3H_6$, Y=O, $R_1$=acryl or methacryl radical, $R_3$=H, $R_4$=H, $R_5$=H in the general formula I.

A further embodiment for an UV absorber in terms of the ophthalmologic composition according to the invention is coumarin-6,7-dipropoxymethacrylate. This one too, can be represented in simple synthetic way in a 2-step reaction analogous to the coumarin-7-propoxymethacrylate. The 6,7-dihydroxycoumarin required to this is also commercially available. In this manner, a compound can be produced, in which an additional methacrylate anchor group has been introduced. The linkage of this second anchor group via an alkoxy spacer has only little influence on the spectral properties of the absorber, but allows to employ it also as a crosslinker in the production of the lens material.

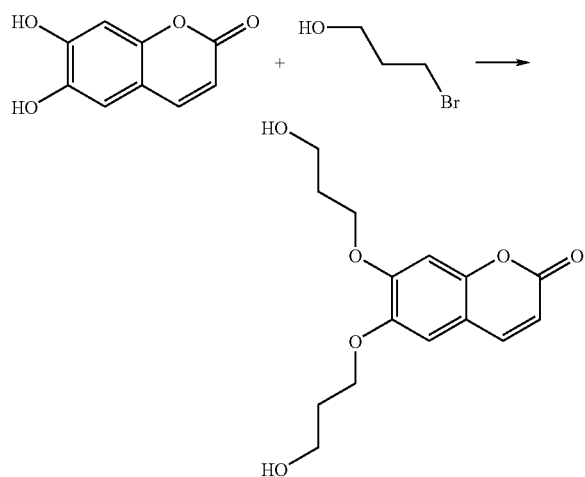

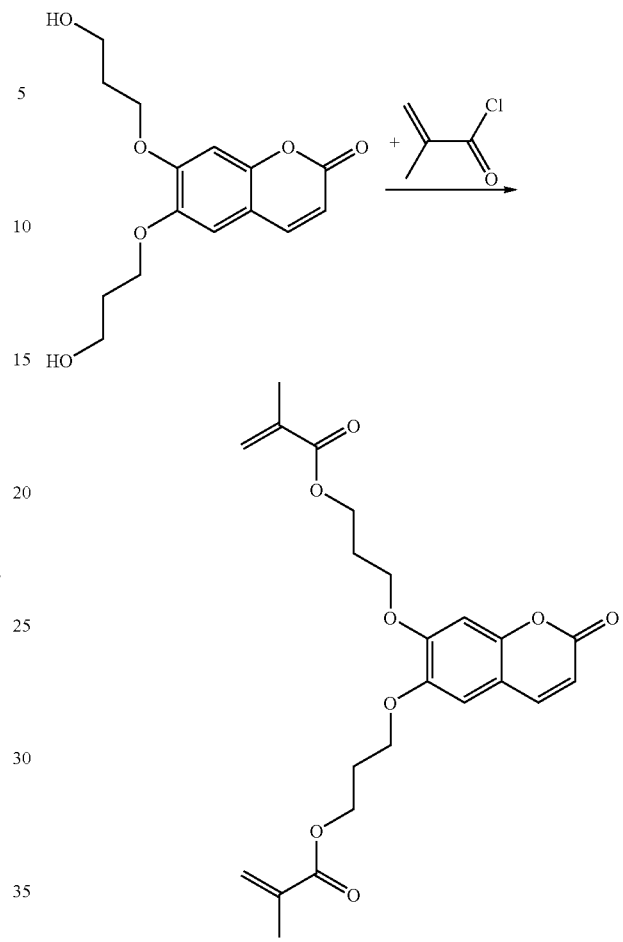

Example 2 n=1, m=0, X=O, $R_2$=—$CH_2$—$CH(OR_1)CH_2$—, Y=O, R1, =acryl or methacryl radical, $R_3$=H, $R_4$=H, $R_5$=H of the general formula I.

A further possibility of producing an UV absorber with two anchor groups results from the use of a branched dihydroxy-halide. If one reacts 7-hydroxycoumarin in a first step with commercially available 3-bromo-1,2-propanediol and subsequently acrylates or methacrylates the resulting alkoxydiol, one obtains a further bifunctional UV absorber.

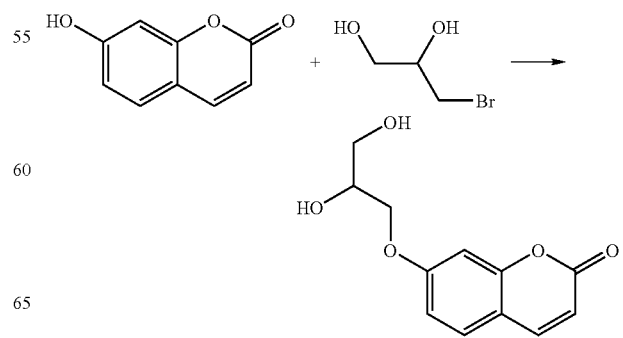

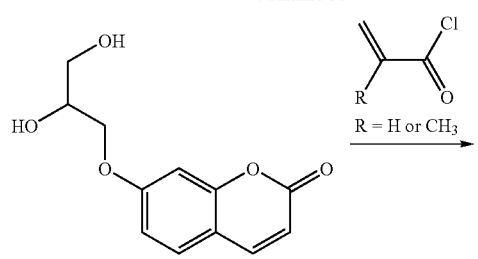

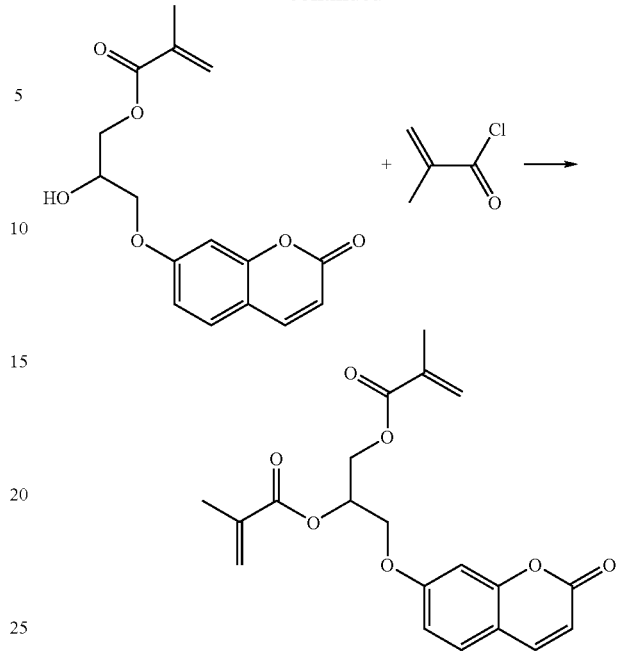

Example 3 n=1, m=0, X=O, $R_2$=—$CH_2$—CH(OR1)$CH_2$—, Y=O, $R_1$=methacryl radical, $R_3$=H, $R_4$=H, $R_5$=H of the general formula I.

If one reacts 7-hydroxycoumarin not with acrylic acid or methacrylic acid chloride, but with commercially available glycidyl methacrylate, thus, one obtains a further UV filter in a single reaction step, in which the coumarin base body is separated from the methacrylate radical by an aliphatic chain. By subsequent esterification with methacryloyl chloride, a further methacrylate function can be introduced at the secondary alcohol group.

Example 4 n=1, m=0, X=O, $R_2$=$C_3H_6$, Y=O, $R_1$=acryl or methacryl radical, $R_3$=H, $R_4$=H, $R_5$=$C_3H_7$ of the general formula I.

Here, $R_5$ is a propyl group having a weak inductive effect (+I effect). The introduction of an additional propyl group into the previously described preferred UV absorber can be managed synthetically without any problems and modifies the spectral properties of the chromophore only to a small extent. If one does not employ 7-hydroxycoumarin in the synthesis, but the also commercially available 7-hydroxy-4-propylcoumarin, one obtains a coumarin derivative after the methacrylation, which differs from the preferred UV absorber by only one propyl side chain.

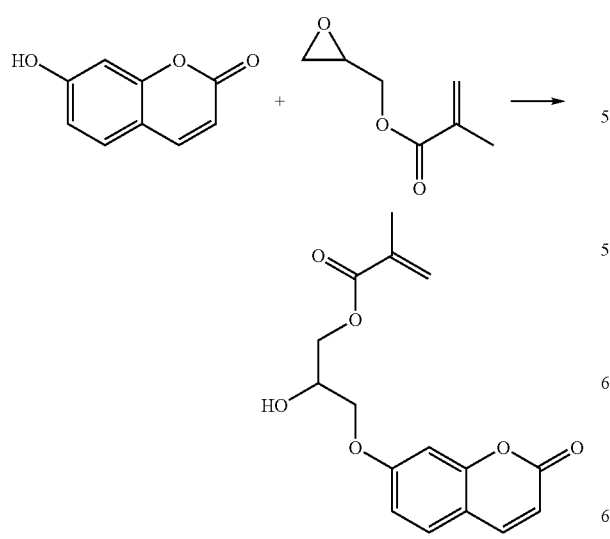

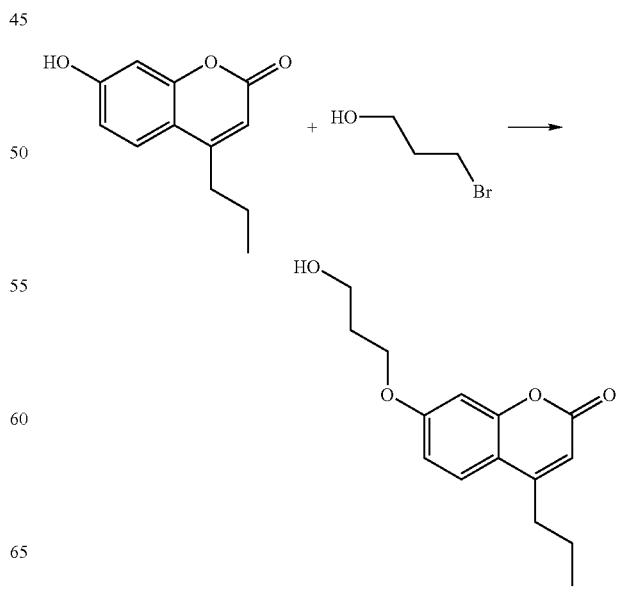

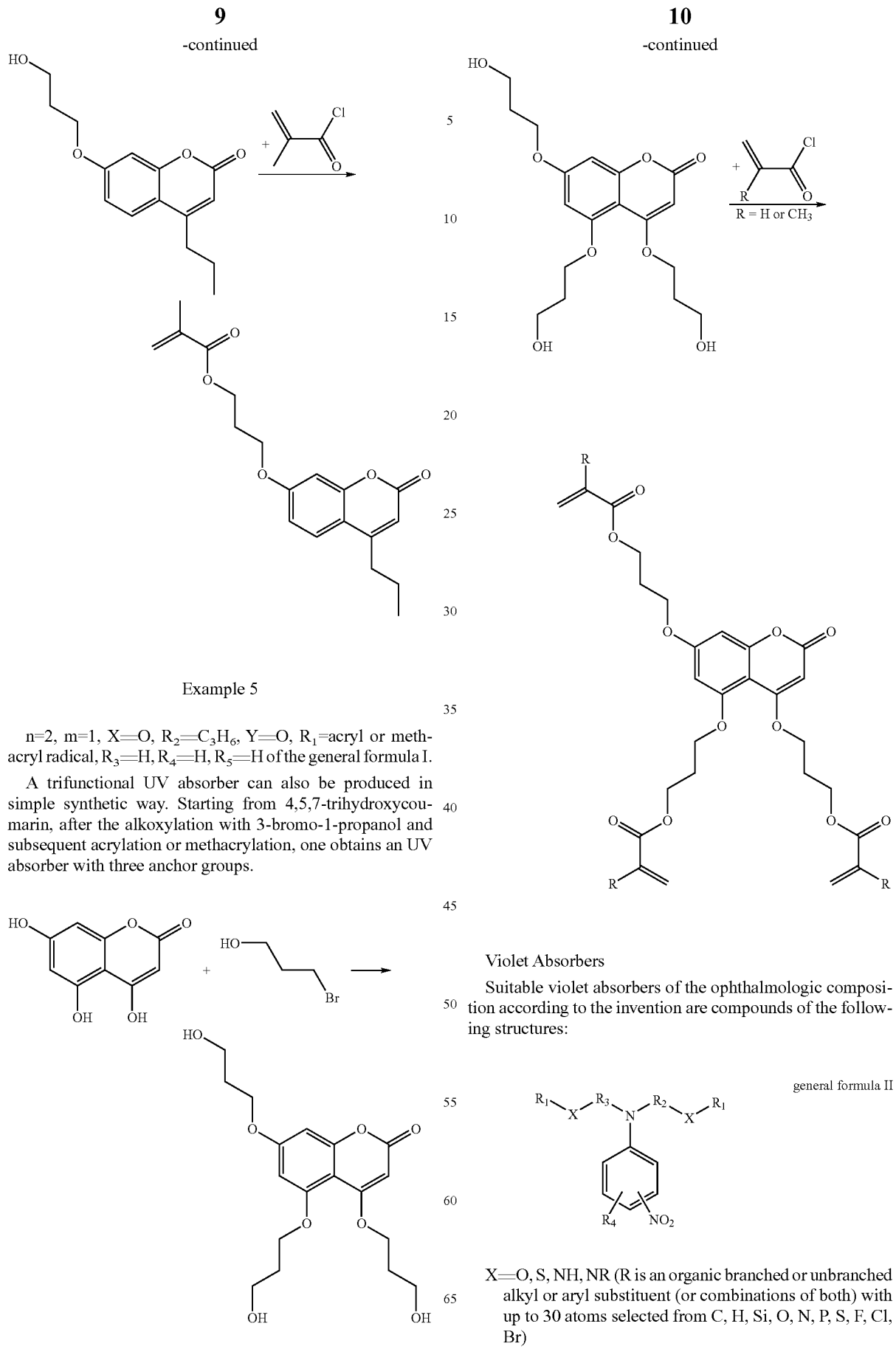

Example 5 n=2, m=1, X=O, R$_2$=C$_3$H$_6$, Y=O, R$_1$=acryl or methacryl radical, R$_3$=H, R$_4$=H, R$_5$=H of the general formula I.

A trifunctional UV absorber can also be produced in simple synthetic way. Starting from 4,5,7-trihydroxycoumarin, after the alkoxylation with 3-bromo-1-propanol and subsequent acrylation or methacrylation, one obtains an UV absorber with three anchor groups.

Violet Absorbers

Suitable violet absorbers of the ophthalmologic composition according to the invention are compounds of the following structures:

general formula II

X=O, S, NH, NR (R is an organic branched or unbranched alkyl or aryl substituent (or combinations of both) with up to 30 atoms selected from C, H, Si, O, N, P, S, F, Cl, Br)

$R_1$=acryl or methacryl radical

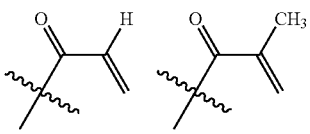

$R_2$=Organic branched and unbranched alkyl or aryl spacer group (or combination of both) with up to 30 atoms selected from: C, H, Si, O, N, P, S, Cl, Br, F $R_3$=organic branched or unbranched alkyl or aryl substituent (or combination of both) with up to 30 atoms selected from: C, H, Si, O, N, P, S, Cl, Br, F $R_4$=H or organic branched or unbranched alkyl or aryl substituent (or combination of both) with up to 30 atoms selected from: C, H, Si, O, N, P, S, Cl, Br, F or further nitro group, alkoxy group or nitrile group Examples of corresponding structures (all stereoisomers or racemic mixtures are included) are:

Structure 1

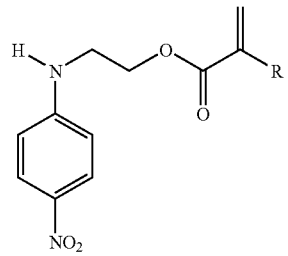

Structure 2

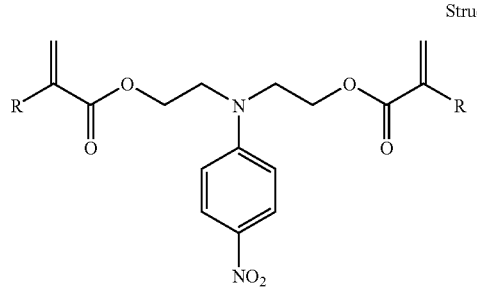

Structure 3

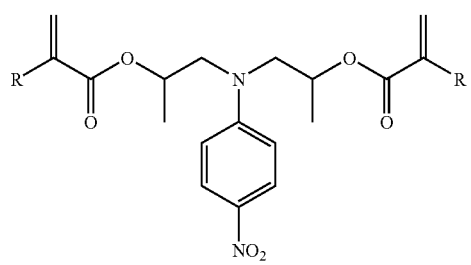

R = H or CH$_3$

Further, suitable violet absorbers are stereoisomers or racemic mixtures of compounds of the following structures:

general formula III

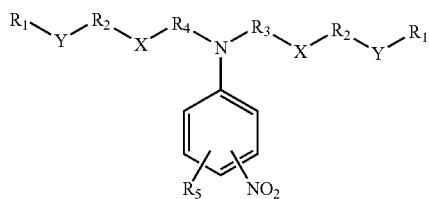

X=O, S, NH, NR (R is an organic branched or unbranched alkyl or aryl substituent (or combinations of both) with up to 30 atoms selected from C, H, Si, O, N, P, S, F, Cl, Br)

Y=O, S, NH, NR (R is an organic branched or unbranched alkyl or aryl substituent (or combinations of both) with up to 30 atoms selected from C, H, Si, O, N, P, S, F, Cl, Br)

$R_1$=acryl or methacryl radical

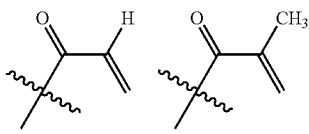

$R_2$=Organic branched or unbranched alkyl or aryl spacer group (or combination of both) with up to 30 atoms selected from: C, H, Si, O, N, P, S, Cl, Br, F $R_3$=Organic branched or unbranched alkyl or aryl spacer group (or combination of both) with up to 30 atoms selected from: C, H, Si, O, N, P, S, Cl, Br, F $R_4$=organic branched or unbranched alkyl or aryl substituent (or combination of both) with up to 30 atoms selected from: C, H, Si, O, N, P, S, Cl, Br, F $R_5$=H or organic branched or unbranched alkyl or aryl substituent with up to 30 atoms selected from: C, H, Si, O, N, P, S, Cl, Br, F or further nitro group, alkoxy group or nitrile group Examples of corresponding structures (all stereoisomers or racemic mixtures are included) are:

Structure 4

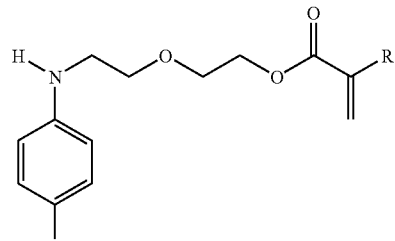

Structure 5

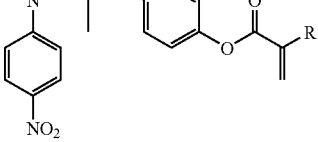

R = H or CH$_3$

A preferred dye for the violet absorber of the ophthalmologic composition according to the invention is:

N,N-Di-2'-ethylmethacrylate-4-nitroaniline having the structure:

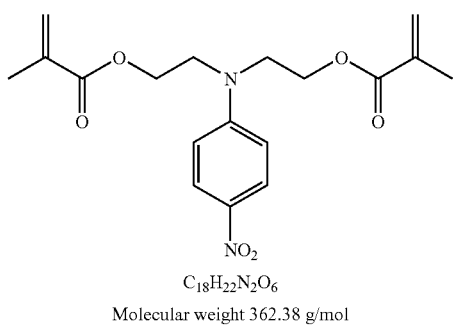

$C_{18}H_{22}N_2O_6$

Molecular weight 362.38 g/mol

The production of this compound is effected in two steps (according to unexamined application EP 0321891 A2), wherein both educts, both the 4-fluoronitrobenzene and the diethanolamine, are commercially available:

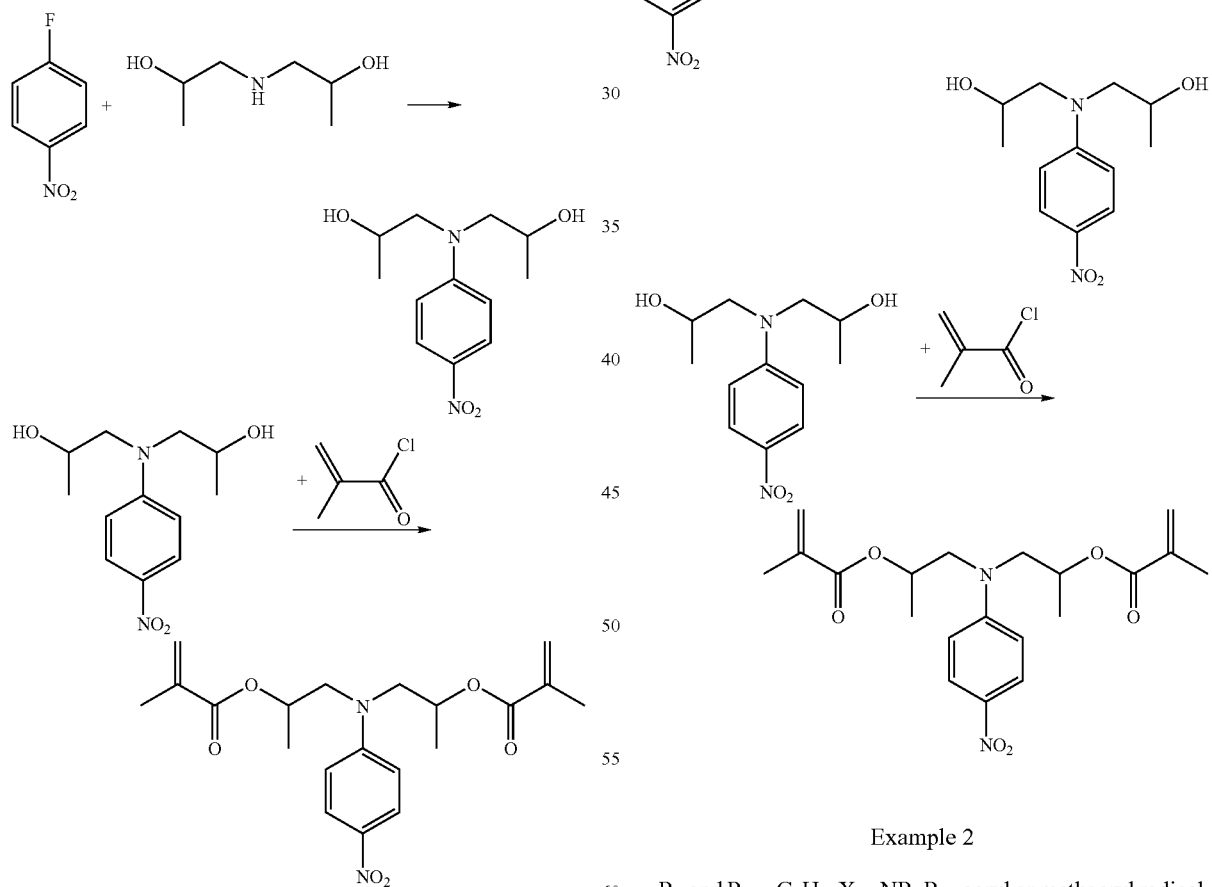

The methacryl radicals serve for covalent bond of the violet filter in a carrier material, in particular lens material based on acrylate. Due to the bifunctionality, the incorporation proceeds quantitatively and thus considerably more effective than in the monofunctional violet filters available on the market.

Further embodiments for the violet absorber are also compounds, in which a nitroanline base body is connected to one or more acryl or methacryl radicals via various spacers.

Embodiments Violet Absorbers

Example 1

$R_2$ and $R_3$=—$CH_2$—$CH(CH_3)$—$X$=O, $R_1$=acryl or methacryl radical, $R_4$=H of the general formula II.

A further embodiment for a yellow chromophore/violet filter is N,N-di-2'-isopropylmethacrylate-4-nitroaniline. This one too, can be produced in simple synthetic way in a 2-step reaction analogous to the diethylmethacrylate-4-nitroaniline. The diisopropanolamine required to this is also commercially available. In this manner, a compound can be produced, which differs from the preferred filter respectively by only one $CH_3$ group in the side chain. By the positive inductive effect of the methyl groups, this chromophore absorbs slightly shifted to longer wavelengths.

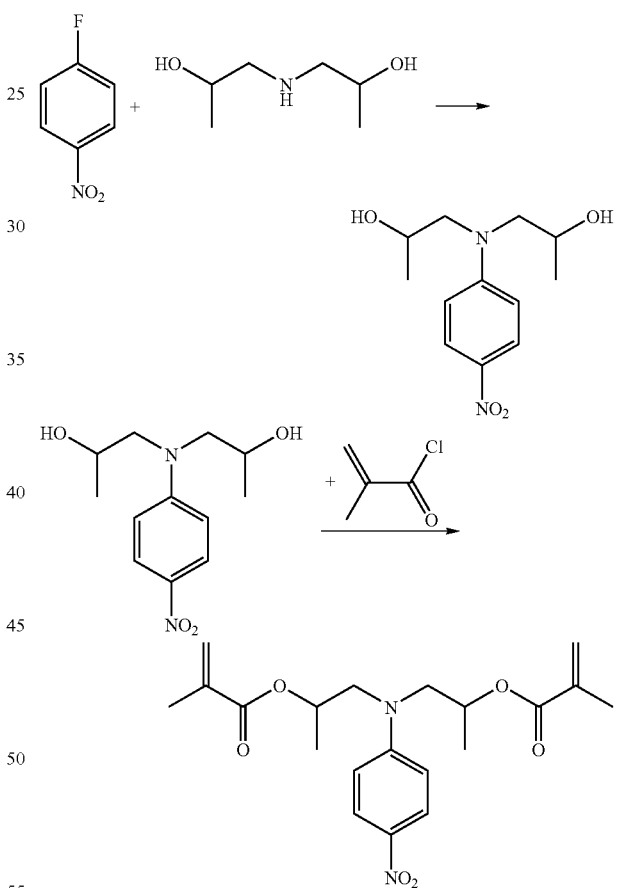

Example 2

$R_2$ and $R_3$=$C_2H_4$, X=NR, $R_1$=acryl or methacryl radical, $R_4$=H of the general formula II.

In this example, N,N-dihydroxyethyl-4-nitroaniline is reacted into the diamino derivative by a simple synthetic method. This diamine can be converted into the diamide by a reaction with acrylic acid chloride. The structure of the chromophore remains unchanged and is separated from the acryl amide by two methylene units.

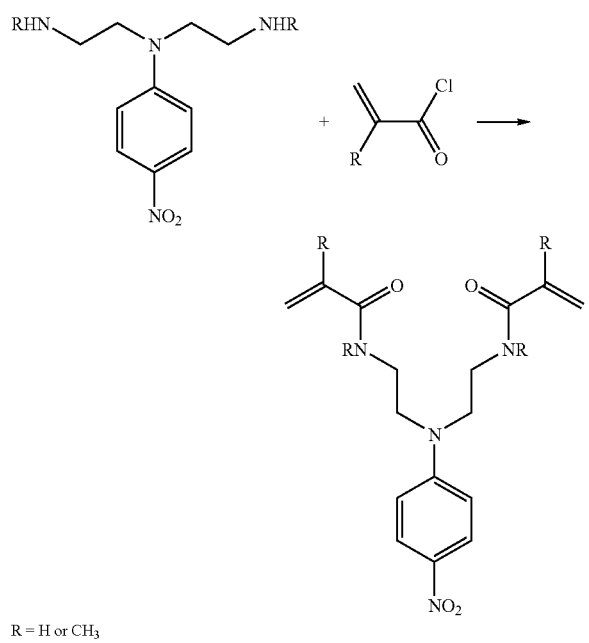

R = H or CH₃

Example 3

$R_3$ and $R_4=C_2H_4$, $X=O$, $R_2=-CH_2-CH(OH)CH_2-$, $Y=O$, $R_1=$acryl or methacryl radical, $R_5=H$ of the general formula III.

If one reacts N,N-dihydroxyethyl-4-nitroaniline not with acrylic acid or methacrylic acid chloride, but with commercially available glycidyl methacrylate, thus, one obtains a further violet filter in a single reaction step, in which the chromophore is separated from the methacrylate radicals by aliphatic chains.

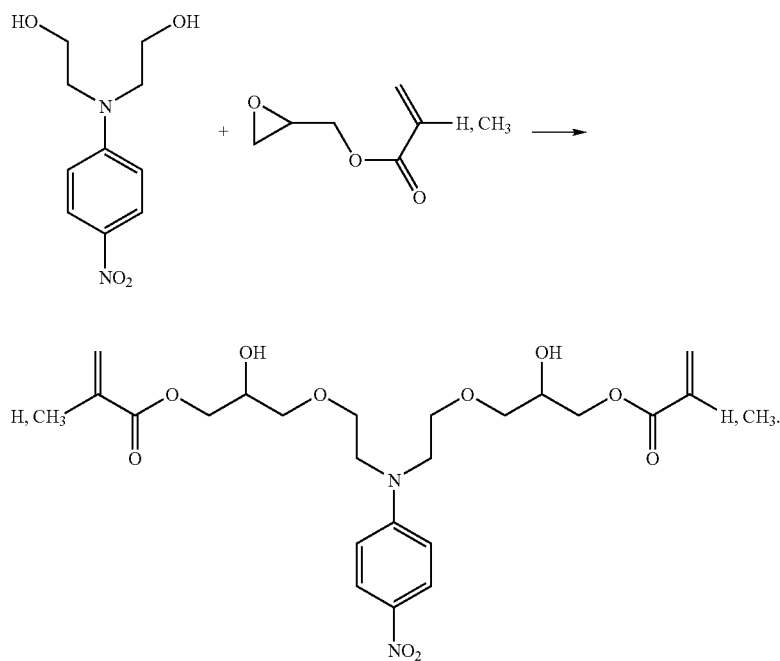

Example 4

$R_2$ and $R_3=C_2H_4$, $X=O$, $R_1=$acryl or methacryl radical, $R_4=CH_3$ of the general formula II.

Here, $R_4$ is a methyl group, which has a weak inductive effect (+I effect). The incorporation of an additional methyl group in the previously described preferred violet filter can be managed synthetically without any problems and modifies the spectral properties of the chromophore only to a small extent. If one reacts diethanolamine not with 4-fluoronitrobenzene, but with the also commercially available 2-fluoro-5-nitrotoluene, thus, a nitroaniline is produced, which differs from the preferred violet absorber by just one additional methyl group at the aniline ring. By esterification with acryloylchloride or methacryloylchloride, thus, a further chromophore with the desired spectral properties is obtained.

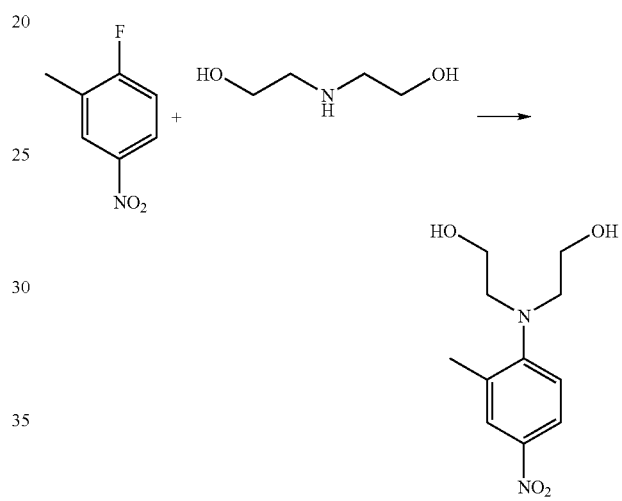

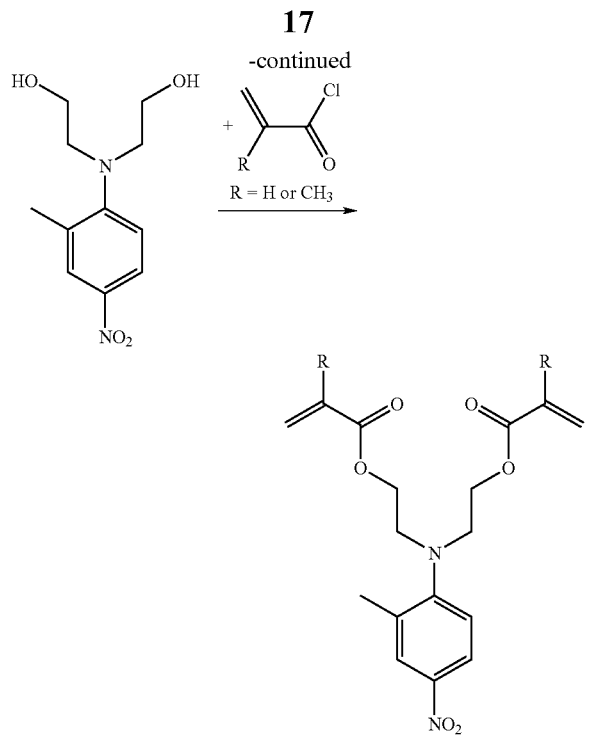

As a biocompatible carrier material, acrylates, in particular with a water content of 1% to 30%, are suitable for the ophthalmologic composition. In the copolymer or in this carrier material, the UV absorber and the violet absorber are covalently bound, respectively. Preferably, the UV absorber is contained in a concentration range of 0.5% to 1.0%. If the ophthalmologic composition is used for an IOL, the respective concentration of the UV absorber is dependent on the respective peak index of refraction (diopter) of the lens. The violet absorber is also covalently bound in the acrylate carrier material or in the copolymer. It can be present in a concentration range of 0.03% to 0.16%. Here too, in use of the ophthalmologic composition for an IOL, the concentration of the violet absorber is directly dependent on the diopter of the lens.

The risk of elution of the absorbers from the carrier matrix does not exist since both the UV absorber according to the invention and the violet filter quantitatively incorporate into the lens material due to the fact that they bear two polymerizable terminal groups.

Suitable biocompatible carrier materials for the UV absorber or the violet absorber are for example hydroxyethyl methacrylate (HEMA), methyl methacrylate (MMA), ethoxyethyl methacrylate (EOEMA), ethoxyethoxy ethylacrylate (EEEA), tetrahydrofufuryl methacrylate (THFMA), tetrahydrofufuryl acrylate (THFA), 2-hydroxypropyl methacrylate (HPMA), 2-hydroxypropyl acrylate (HPA), 2-hydroxyethyl acrylamide, 2-hydroxyethyl methacrylamide, methoxyethyl methacrylate (MOEMA) and methoxyethyl acrylate (MOEA). From the above mentioned substances, copolymers can be produced, possibly using a cross-linker, and used as a carrier material. The percentage composition of the monomers is variable in a wide range. The carrier materials can be adjusted hydrophilic with a water content of for example 1% to 30% or hydrophobic. A limiting factor in hydrophobic, anhydrous polymers is the glass transition temperature. It can be in the range between 0° C. and 11° C. Moreover, it is important that hydrophilic polymers have sufficient flexibility after swelling.

Embodiments of the ophthalmologic composition are the following with quantitative compositions in % by weight.

Embodiment Carrier Materials

Example 1

Hydrophobic

EOEMA (ethoxyethyl methacrylate) 85-97% by wt.
MMA (methyl methacrylate) 0-15% by wt.
EEEA (ethoxyethoxy ethylacrylate) 0-5% by wt.
EGDMA (ethylene glycol dimethacrylate) 0-0.7% by wt.
UV absorber 0.1-1.0% by wt.
Violet absorber 0.03-0.16% by wt.

Example 2

Hydrophilic

HEMA (hydroxyethyl methacrylate) 50-85% by wt.
EDEMA (ethoxyethyl methacrylate) 30-40% by wt.
THFMA (tetrahydrofufuryl methacrylate) 5-20% by wt.
EGDMA (ethylene glycol dimethacrylate) 0-0.7% by wt.
UV absorber 0.1-1.0% by wt.
Violet absorber 0.03-0.16% by wt.

For the synthesis of the respective lens materials, first, the monomers are consecutively weighed in a beaker and stirred until a homogenous solution has developed. Thereafter, first, the cross-linker and subsequently the violet as well as the UV absorber are added. With slight heating, it is again stirred until a homogenous solution is obtained.

The mixture respectively resulting is mixed with a suitable initiator and converted into the polymerization shapes (e.g. cups, rod or flat shapes). The polymerization is initiated by heating (60° C. for 12-16 h). After cooling, the polymerizates are removed, optionally post-cured in the compartment dryer and brought to the desired blank size by turning and milling (e.g. 3 mm thickness, 12.7 mm diameter).

Transmission measurements show that with the aid of the ophthalmologic composition according to the invention, it is absorbed not only the UV portion (<400 nm), but also the entire violet light portion (400 nm to 430 nm). Ophthalmologic compositions on the market have a high light transmission in the violet range with a transmission up to one third. The composition according to the invention only shows a transmission of below 3% at 430 nm.

In the blue light range, for example, the composition according to the invention has a light transmission of above 70% at 460 nm, whereas the known lenses here only have a transmission of 50-60%.

The ophthalmologic composition is in particular suitable for visual aids such as glasses, contact lenses and eye implants. In particular, the ophthalmologic composition according to the invention is suitable for intraocular lenses.

The invention claimed is:

1. An ophthalmologic composition, which is constructed based on acrylate and/or methacrylate and which has an UV absorber, in which one or more acrylic acid or methacrylic acid units are bound to a substituted or unsubstituted coumarin base structure via an alkyl spacer, as well as contains a violet absorber (yellow dye) based on an N-alkoxyacrylated or N-alkoxymethacrylated or based on an N,N-dialkoxyacrylated or N,N-dialkoxymethacrylated substituted or unsubstituted nitroaniline, wherein the UV absorber is included in a concentration range of 0.5% to 1.0%.

2. The ophthalmologic composition according to claim 1, in which the UV absorber is a stereoisomer or a racemic mixture of the following structure:

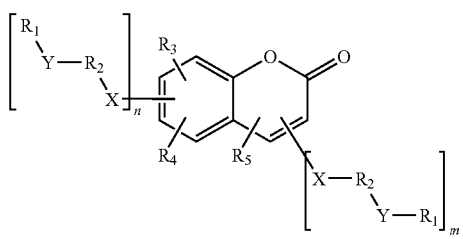

wherein

R1 is an acryl or methacryl radical;

R2: organic branched and unbranched alkyl or aryl substituents (or combinations of both) with up to 30 atoms selected from the group consisting of C, H, Si, O, N, P, S, F, Cl, and Br;

R3, R4 and R5: H or organic branched and unbranched alkyl or aryl substituents (or combinations of both) with up to 30 atoms selected from the group consisting of C, H, Si, O, N, P, S, F, Cl, and Br;

X and Y: O, S, NH, NR(R is an organic branched or unbranched alkyl or aryl substituent (or combinations of both) with up to 30 atoms selected from the group consisting of C, H, Si, O, N, P, S, F, Cl, and Br); and n=0 to 2 as well as m=0 or 1, wherein n+m is always greater than or equal to 1.

3. The ophthalmologic composition according to claim 2, wherein n=1, m=0, X=O, R2=C3H6, Y=O, R1=acryl or methacryl radical, R3=H, R4=H, R5=H with the structure:

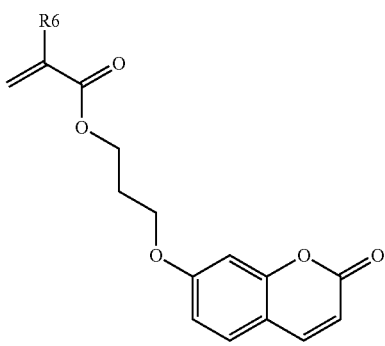

where R6=H or CH$_3$.

4. The ophthalmologic composition according to claim 2, wherein n=2, m=0, X=O, R2=C3H6, Y=O, R1=acryl or methacryl radical, R3=H, R4=H, R5=H with the structure:

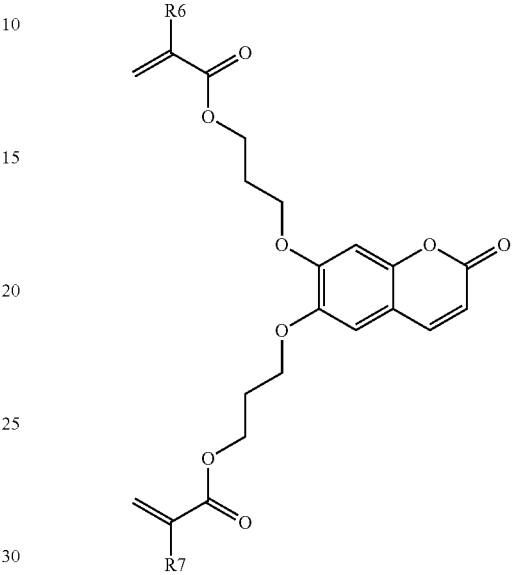

where R6=H or CH$_3$ and R7=H or CH$_3$.

5. The ophthalmologic composition according to claim 2, wherein n=1, m=0, X=O, R2=—CH2-CH(OR1)CH2-, Y=O, R1=acryl or methacryl radical, R3=H, R4=H, R5=H with the structure:

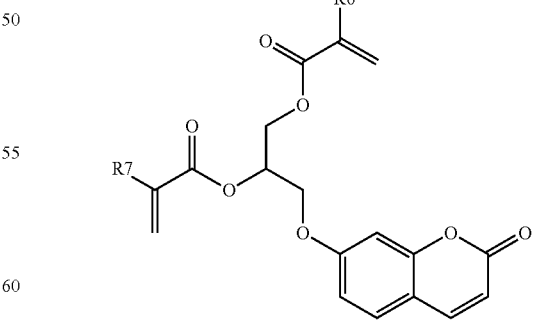

where R6=H or CH$_3$ and R7=H or CH$_3$.

6. The ophthalmologic composition according to claim 2, wherein n=1, m=0, X=O, R2=—CH2-CH(OH)CH2-, Y=O, R1=acryl or methacryl radical, R3=H, R4=H, R5=H with the structure:

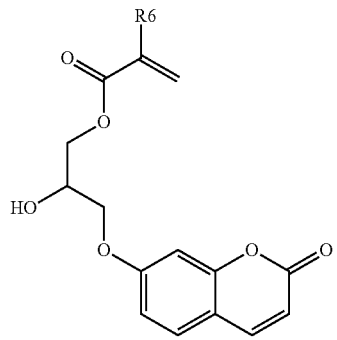

where R6=H or CH$_3$.

7. The ophthalmologic composition according to claim 2, wherein n=1, m=0, X=O, R2=C3H6, Y=O, R1=acryl or methacryl radical, R3=H, R4=H, R5=C3H7 with the structure:

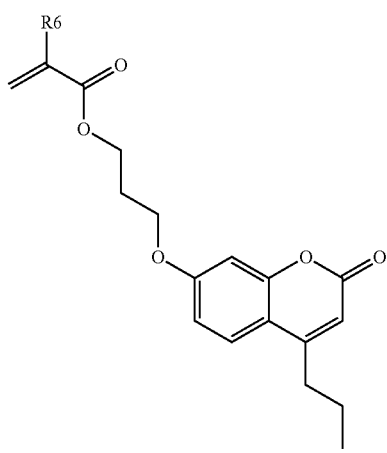

where R6=H or CH$_3$.

8. The ophthalmologic composition according to claim 2, wherein n=2, m=1, X=O, R2=C3H6, Y=O, R1=acryl or methacryl radical, R3=H, R4=H, R5=H with the structure:

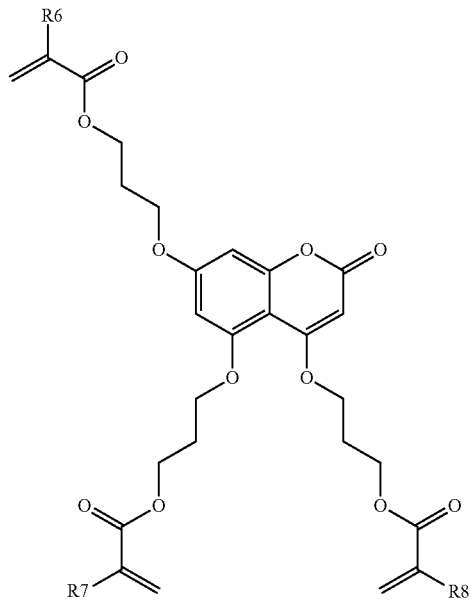

where R6=H or CH$_3$, R7=H or CH$_3$, and R8=H or CH$_3$.

9. The ophthalmologic composition according to claim 1, wherein the violet absorber is a stereoisomer or a racemic mixture of dyes of the following structure:

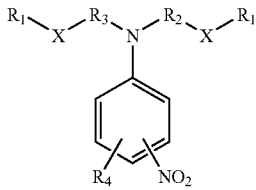

wherein
- R1 is an acryl or methacryl radical;
- R2: organic branched and unbranched alkyl or aryl spacer group (or combinations of both) with up to 30 atoms selected from the group consisting of C, H, Si, O, N, P, S, F, Cl, and Br;
- R3: organic branched and unbranched alkyl or aryl substituent (or combinations of both) with up to 30 atoms selected from the group consisting of C, H, Si, O, N, P, S, F, Cl, and Br;
- R4: H or organic branched and unbranched alkyl or aryl substituent (or combinations of both) with up to 30 atoms selected from C, H, Si, O, N, P, S, F, Cl, Br or further nitro group, alkoxy group or nitrile group; and
- X: O, S, NH, NR(R is an organic branched or unbranched alkyl or aryl substituent (or combinations of both) with up to 30 atoms selected from the group consisting of C, H, Si, O, N, P, S, F, Cl, and Br).

10. The ophthalmologic composition according to claim 1, wherein the violet absorber is a stereoisomer or a racemic mixture of dyes of the following structure:

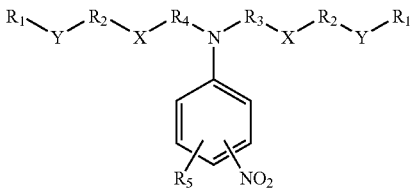

wherein
R1 is an acryl or methacryl radical;
R2: organic branched and unbranched alkyl or aryl spacer groups (or combinations of both) with up to 30 atoms selected from the group consisting of C, H, Si, O, N, P, S, F, Cl, and Br;
R3: organic branched and unbranched alkyl or aryl spacer groups (or combinations of both) with up to 30 atoms selected from the group consisting of C, H, Si, O, N, P, S, F, Cl, and Br;
R4: organic branched and unbranched alkyl or aryl substituent (or combinations of both) with up to 30 atoms selected from the group consisting of C, H, Si, O, N, P, S, F, Cl, and Br;
R5: H or organic branched and unbranched alkyl or aryl substituent (or combinations of both) with up to 30 atoms selected from C, H, Si, O, N, P, S, F, Cl, Br or further nitro group, alkoxy group or nitrile group; and
X, Y: O, S, NH, NR(R is an organic branched or unbranched alkyl or aryl substituent (or combinations of both) with up to 30 atoms selected from the group consisting of C, H, Si, O, N, P, S, F, Cl, and Br).

11. The ophthalmologic composition according to claim 9, wherein R2 and R3=C2H4, X=O, R1=acryl or methacryl radical, R4=H with the structure:

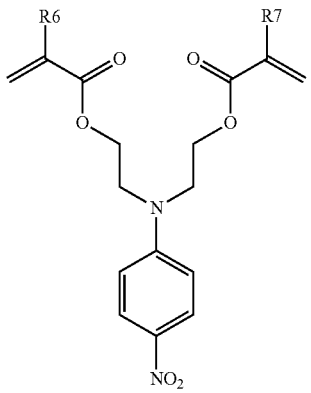

where R6=H or $CH_3$ and R7=H or $CH_3$.

12. The ophthalmologic composition according to claim 9, wherein R2 and R3=—CH2-CH(CH3)-, X=O, R1=acryl or methacryl radical, R4=H with the structure:

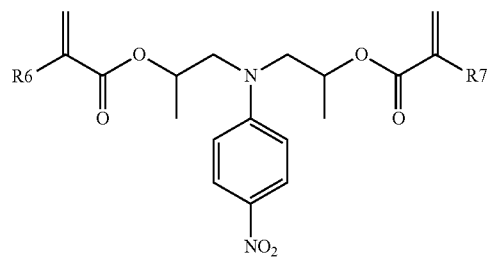

where R6=H or $CH_3$ and R7=H or $CH_3$.

13. The ophthalmologic composition according to claim 9, wherein R2 and R3=C2H4, X=NR, R1=acryl or methacryl radical, R4=H with the structure:

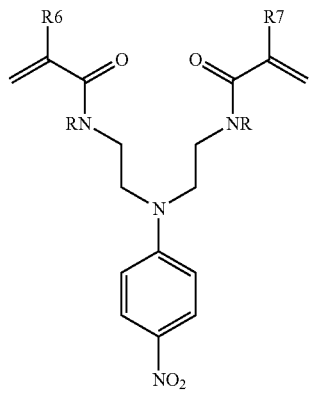

where R6=H or $CH_3$ and R7=H or $CH_3$.

14. The ophthalmologic composition according to claim 10, wherein R3 and R4=C2H4, X=O, R2=—CH2-CH(OH)CH2-, Y=O, R1=acryl or methacryl radical, R5=H with the structure:

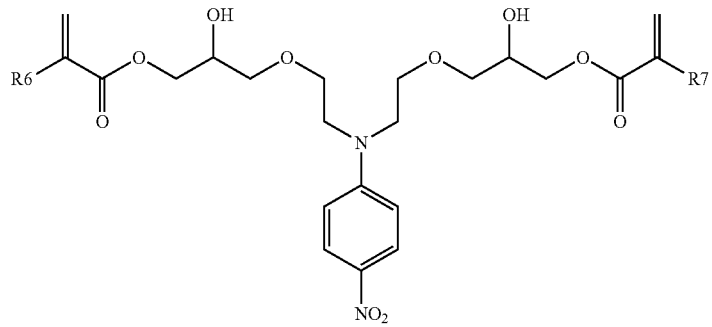

where R6=H or $CH_3$ and R7=H or $CH_3$.

15. The ophthalmologic composition according to claim 9, wherein R2 and R3=C2H4, X=O, R1=acryl or methacryl radical, R4=CH3 with the structure:

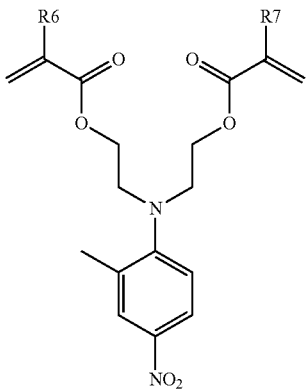

where R6=H or CH$_3$ and R7=H or CH$_3$.

16. The ophthalmologic composition according to claim 1, wherein the UV absorber and the violet absorber are provided in a biocompatible carrier substance.

17. The ophthalmologic composition according to claim 16, wherein the carrier substance is composed of at least one acrylate.

18. The ophthalmologic composition according to claim 17, wherein the UV absorber and the violet absorber are covalently bound in the acrylate material.

19. The ophthalmologic composition according to claim 17, wherein the at least one acrylate is a hydrophilic material with a water content of 1% to 30%.

20. The ophthalmologic composition according to claim 17, wherein the at least one acrylate is or are HEMA and/or MMA.

21. The ophthalmologic composition according to claim 16, containing as a carrier substance:

| | |
|---|---|
| EOEMA (ethoxyethyl methacrylate) | 85-97% by wt.; |
| MMA (methyl methacrylate) | 0-15% by wt.; |
| EEEA (ethoxyethoxy ethylacrylate) | 0-5% by wt.; |
| EGDMA (ethylene glycol dimethacrylate) | 0-0.7% by wt.; |
| UV absorber | 0.1-1.0% by wt.; and |
| Violet absorber | 0.03-0.16% by wt. |

22. The ophthalmologic composition according to claim 16, containing as a carrier substance:

| | |
|---|---|
| HEMA (hydroxyethyl methacrylate) | 50-85% by wt.; |
| EOEMA (ethoxyethyl methacrylate) | 30-40% by wt.; |
| THFMA (tetrahydrofurfuryl methacrylate) | 5-20% by wt.; |
| EGDMA (ethylene glycol dimethacrylate) | 0-0.7% by wt.; |
| UV absorber | 0.1-1.0% by wt.; and |
| Violet absorber | 0.03-0.16% by wt. |

23. A method for producing an ophthalmologic lens, the method comprising providing an ophthalmologic composition according to claim 1.

24. A method for producing an ophthalmologic implant, the method comprising providing an ophthalmologic composition according to claim 1.

25. A method for producing an intraocular lens, the method comprising providing the ophthalmologic composition according to claim 1.

26. An eye implant comprising implant material having the ophthalmologic composition according to claim 1.

27. The eye implant according to claim 26, which is formed as an intraocular lens.

* * * * *